United States Patent
Horvath et al.

(10) Patent No.: US 7,384,932 B2
(45) Date of Patent: Jun. 10, 2008

(54) δD-CRYSTALLINE FORM OF IVABRADINE HYDROCHLORIDE, A PROCESS FOR ITS PREPARATION AND PHARMACEUTICAL COMPOSITIONS CONTAINING IT

(75) Inventors: Stephane Horvath, La-Chapelle-Saint-Mesmin (FR); Marie-Noelle Auguste, Orleans (FR); Gerard Damien, Meung-sur-Loire (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 11/545,362

(22) Filed: Oct. 10, 2006

(65) Prior Publication Data

US 2007/0082886 A1  Apr. 12, 2007

(30) Foreign Application Priority Data

Oct. 11, 2005 (FR) .................................. 05 10354

(51) Int. Cl.
C07D 223/16 (2006.01)
A61K 31/55 (2006.01)
A61P 9/10 (2006.01)

(52) U.S. Cl. .................. 514/212.07; 540/523
(58) Field of Classification Search ................ 540/523; 514/212.07
See application file for complete search history.

(56) References Cited

U.S. PATENT DOCUMENTS 5,296,482 A  3/1994  Peglion et al.
2005/0228177 A1  10/2005  Lerestif et al.

FOREIGN PATENT DOCUMENTS

EP  0543859  3/1993
FR  2868777  10/2005

OTHER PUBLICATIONS

"Ivabradine Hydrochloride Antianginal HCN (LF Current) Blocker", Drugs of the Future, pp. 652-658, 2003.
French Preliminary Search Report for FR0510354 of Jun. 26, 2006.
Ferrari, et al., *European Heart Journal Supplements*, 2005, 7 (Supplement H), H16-H21.
Fox, *European Heart Journal Supplements*, 2005, 7 (Supplement H), H33-H36.

*Primary Examiner*—Bruck Kifle
(74) *Attorney, Agent, or Firm*—Hueschen and Sage

(57) ABSTRACT

A δd-crystalline form of ivabradine hydrochloride of formula (I):

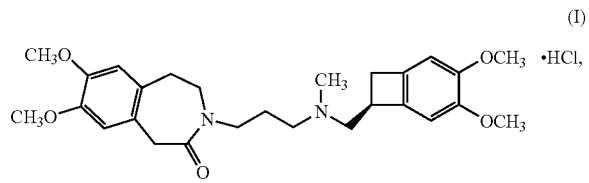

characterised by its powder X-ray diffraction data.

Medicinal products containing the same which are useful as bradycardics.

5 Claims, No Drawings

δD-CRYSTALLINE FORM OF IVABRADINE HYDROCHLORIDE, A PROCESS FOR ITS PREPARATION AND PHARMACEUTICAL COMPOSITIONS CONTAINING IT

The present invention relates to the δd-crystalline form of ivabradine hydrochloride of formula (I)

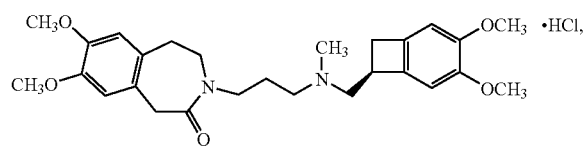

to a process for its preparation and to pharmaceutical compositions containing it.

Ivabradine, and addition salts thereof with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarct and associated rhythm disturbances, and also in various pathologies involving rhythm disturbances, especially supraventricular rhythm disturbances, and in heart failure.

The preparation and therapeutic use of ivabradine and addition salts thereof with a pharmaceutically acceptable acid, and more especially its hydrochloride, have been described in the European patent specification EP 0 534 859.

In view of the pharmaceutical value of this compound, it has been of prime importance to obtain it with excellent purity. It has also been important to be able to synthesise it by means of a process that can readily be converted to the industrial scale, especially in a form that allows rapid filtration and drying. Finally, that form had to be perfectly reproducible, easily formulated and sufficiently stable to allow its storage for long periods without particular requirements for temperature, light or oxygen level.

The patent specification EP 0 534 859 describes a synthesis process for ivabradine and its hydrochloride. However, that document does not specify the conditions for obtaining ivabradine in a form that exhibits those characteristics in a reproducible manner.

The Applicant has now found that a particular salt of ivabradine, the hydrochloride, can be obtained in a well defined crystalline form that exhibits valuable characteristics for stability and processability.

More specifically, the present invention relates to the δd-crystalline form of ivabradine hydrochloride, characterised by the following powder X-ray diffraction diagram, measured using a PANalytical X'Pert Pro diffractometer together with an X'Celerator detector and expressed in terms of line position (Bragg's angle 2 theta, expressed in degrees), line height (expressed in counts), line area (expressed in counts x degrees), line width at half-height ("FWHM", expressed in degrees) and interplanar distance d (expressed in Å):

| Line no. | Angle 2 theta (degrees) | Height (counts) | Area (counts × degrees) | FWHM (degrees) | Interplanar distance (Å) |
|---|---|---|---|---|---|
| 1 | 4.1 | 414 | 41 | 0.1004 | 21.672 |
| 2 | 6.8 | 176 | 139 | 0.8029 | 13.078 |
| 3 | 8.6 | 1020 | 101 | 0.1004 | 10.305 |
| 4 | 9.1 | 323 | 43 | 0.1338 | 9.687 |
| 5 | 10.9 | 224 | 30 | 0.1338 | 8.100 |
| 6 | 11.7 | 354 | 47 | 0.1338 | 7.592 |
| 7 | 14.6 | 2774 | 458 | 0.1673 | 6.074 |
| 8 | 15.3 | 1805 | 328 | 0.184 | 5.800 |
| 9 | 16.6 | 986 | 163 | 0.1673 | 5.345 |
| 10 | 17.2 | 3821 | 946 | 0.2509 | 5.153 |
| 11 | 18.1 | 2290 | 378 | 0.1673 | 4.898 |
| 12 | 19.1 | 440 | 73 | 0.1673 | 4.649 |
| 13 | 19.6 | 289 | 38 | 0.1338 | 4.526 |
| 14 | 20.1 | 650 | 86 | 0.1338 | 4.408 |
| 15 | 20.9 | 887 | 146 | 0.1673 | 4.252 |
| 16 | 21.4 | 3112 | 565 | 0.184 | 4.147 |
| 17 | 22.1 | 1708 | 254 | 0.1506 | 4.027 |
| 18 | 22.5 | 1191 | 275 | 0.2342 | 3.945 |
| 19 | 23.4 | 619 | 102 | 0.1673 | 3.800 |
| 20 | 23.9 | 1343 | 222 | 0.1673 | 3.728 |
| 21 | 24.7 | 256 | 34 | 0.1338 | 3.604 |
| 22 | 25.6 | 309 | 41 | 0.1338 | 3.482 |
| 23 | 26.2 | 1899 | 313 | 0.1673 | 3.397 |
| 24 | 26.9 | 1588 | 183 | 0.1171 | 3.310 |
| 25 | 27.6 | 1357 | 224 | 0.1673 | 3.231 |
| 26 | 29.1 | 140 | 37 | 0.2676 | 3.069 |
| 27 | 29.5 | 145 | 29 | 0.2007 | 3.023 |

The invention relates also to a process for the preparation of the δd-crystalline form of ivabradine hydrochloride, which process is characterised in that acetonitrile or a mixture of acetonitrile and water is preheated, ivabradine hydrochloride is added, the solution obtained is allowed to cool at room temperature, held at room temperature until crystallisation is complete, and the crystals formed are dehydrated.

In the crystallisation process according to the invention it
  is possible to use ivabradine hydrochloride obtained by
  any process, for example ivabradine hydrochloride
  obtained by the preparation process described in patent
  specification EP 0 534 859.

The solution may advantageously be seeded during the
  cooling step.

The acetonitrile or mixture of acetonitrile and water is
  preferably preheated to a temperature between 60° C.
  and reflux, more preferably between 65 and 75° C.

The dilution is preferably more than 15 ml/g, more
  preferably between 50 and 100 ml/g.

The dehydration is preferably performed by heating.

The invention relates also to pharmaceutical compositions comprising as active ingredient the δd-crystalline form of ivabradine hydrochloride together with one or more appropriate, inert and non-toxic excipients. Among the pharmaceutical compositions according to the invention there may be mentioned, more especially, those that are suitable for oral, parenteral (intravenous or subcutaneous) or nasal administration, tablets or dragées, sublingual tablets, capsules, lozenges, suppositories, creams, ointments, dermal gels, injectable preparations and drinkable suspensions.

The useful dosage can be varied according to the nature and severity of the disorder, the administration route and the age and weight of the patient. The dosage varies from 1 to 500 mg per day in one or more administrations.

The Examples that follow illustrate the invention.

The X-ray powder diffraction spectrum was measured under the following experimental conditions:
PANalytical X'Pert Pro diffractometer, X'Celerator detector, temperature-regulated chamber,
voltage 45 kV, intensity 40 mA,
mounting θ-θ,
nickel (Kβ) filter,
incident-beam and diffracted-beam Soller slit: 0.04 rad,
automatic divergence slits: irradiated length of 10 mm,
mask: 10 mm,
antiscatter slit: ½°,
measurement mode: continuous from 3° to 30°, in increments of 0.017°,
measurement time per step : 19.7 s,
total time: 4 min 32 s,
measurement speed: 0.108°/s.

EXAMPLE 1

δd-crystalline Form of Ivabradine Hydrochloride 160 ml of acetonitrile are preheated to 70° C. and then 2 g of ivabradine hydrochloride obtained according to the process described in patent specification EP 0 534 859 are added, in portions, with stirring until dissolution is complete. The solution is then stored at ambient temperature for 2 days. The crystals are removed by filtration in vacuo and are spread out onto a crystallisation plate. The crystals are then heated to a temperature of 85° C. at a rate of 10° C./min and held at 85° C. for 4 hours.

Powder X-ray Diffraction Diagram:

The powder X-ray diffraction profile (diffraction angles) of the δd-form of ivabradine hydrochloride is given by the significant lines collated in the following table:

| Line no. | Angle 2 theta (degrees) | Height (counts) | Area (counts × degrees) | FWHM (degrees) | Interplanar distance (Å) |
|---|---|---|---|---|---|
| 1 | 4.1 | 414 | 41 | 0.1004 | 21.672 |
| 2 | 6.8 | 176 | 139 | 0.8029 | 13.078 |
| 3 | 8.6 | 1020 | 101 | 0.1004 | 10.305 |
| 4 | 9.1 | 323 | 43 | 0.1338 | 9.687 |
| 5 | 10.9 | 224 | 30 | 0.1338 | 8.100 |
| 6 | 11.7 | 354 | 47 | 0.1338 | 7.592 |
| 7 | 14.6 | 2774 | 458 | 0.1673 | 6.074 |
| 8 | 15.3 | 1805 | 328 | 0.184 | 5.800 |
| 9 | 16.6 | 986 | 163 | 0.1673 | 5.345 |
| 10 | 17.2 | 3821 | 946 | 0.2509 | 5.153 |
| 11 | 18.1 | 2290 | 378 | 0.1673 | 4.898 |
| 12 | 19.1 | 440 | 73 | 0.1673 | 4.649 |
| 13 | 19.6 | 289 | 38 | 0.1338 | 4.526 |
| 14 | 20.1 | 650 | 86 | 0.1338 | 4.408 |
| 15 | 20.9 | 887 | 146 | 0.1673 | 4.252 |
| 16 | 21.4 | 3112 | 565 | 0.184 | 4.147 |
| 17 | 22.1 | 1708 | 254 | 0.1506 | 4.027 |
| 18 | 22.5 | 1191 | 275 | 0.2342 | 3.945 |
| 19 | 23.4 | 619 | 102 | 0.1673 | 3.800 |
| 20 | 23.9 | 1343 | 222 | 0.1673 | 3.728 |
| 21 | 24.7 | 256 | 34 | 0.1338 | 3.604 |
| 22 | 25.6 | 309 | 41 | 0.1338 | 3.482 |
| 23 | 26.2 | 1899 | 313 | 0.1673 | 3.397 |
| 24 | 26.9 | 1588 | 183 | 0.1171 | 3.310 |
| 25 | 27.6 | 1357 | 224 | 0.1673 | 3.231 |
| 26 | 29.1 | 140 | 37 | 0.2676 | 3.069 |
| 27 | 29.5 | 145 | 29 | 0.2007 | 3.023 |

EXAMPLE 2

Pharmaceutical Composition

Formula for the preparation of 1000 tablets each containing 5 mg of ivabradine base:

| | |
|---|---|
| Compound of Example 1 | 5.39 g |
| Maize starch | 20 g |
| Anhydrous colloidal silica | 0.2 g |
| Mannitol | 63.91 g |
| PVP | 10 g |
| Magnesium stearate | 0.5 g |

The invention claimed is:

1. A δd-crystalline form of ivabradine hydrochloride of formula (I):

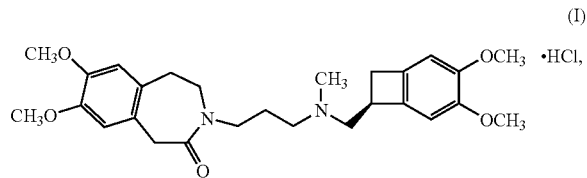

(I)

exhibiting essentially the following powder X-ray diffraction data, measured using a PANalytical X'Pert Pro diffractometer together with an X'Celerator detector and expressed in terms of line position (Bragg's angle 2 theta, expressed in degrees), line height (expressed in counts), line area (expressed in counts × degrees), line width at half-height ("FWHM", expressed in degrees) and interplanar distance d (expressed in Å):

| Line no. | Angle 2 theta (degrees) | Height (counts) | Area (counts × degrees) | FWHM (degrees) | Interplanar distance (Å) |
|---|---|---|---|---|---|
| 1 | 4.1 | 414 | 41 | 0.1004 | 21.672 |
| 2 | 6.8 | 176 | 139 | 0.8029 | 13.078 |
| 3 | 8.6 | 1020 | 101 | 0.1004 | 10.305 |
| 4 | 9.1 | 323 | 43 | 0.1338 | 9.687 |
| 5 | 10.9 | 224 | 30 | 0.1338 | 8.100 |
| 6 | 11.7 | 354 | 47 | 0.1338 | 7.592 |
| 7 | 14.6 | 2774 | 458 | 0.1673 | 6.074 |
| 8 | 15.3 | 1805 | 328 | 0.184 | 5.800 |
| 9 | 16.6 | 986 | 163 | 0.1673 | 5.345 |
| 10 | 17.2 | 3821 | 946 | 0.2509 | 5.153 |
| 11 | 18.1 | 2290 | 378 | 0.1673 | 4.898 |
| 12 | 19.1 | 440 | 73 | 0.1673 | 4.649 |
| 13 | 19.6 | 289 | 38 | 0.1338 | 4.526 |
| 14 | 20.1 | 650 | 86 | 0.1338 | 4.408 |
| 15 | 20.9 | 887 | 146 | 0.1673 | 4.252 |
| 16 | 21.4 | 3112 | 565 | 0.184 | 4.147 |
| 17 | 22.1 | 1708 | 254 | 0.1506 | 4.027 |
| 18 | 22.5 | 1191 | 275 | 0.2342 | 3.945 |
| 19 | 23.4 | 619 | 102 | 0.1673 | 3.800 |
| 20 | 23.9 | 1343 | 222 | 0.1673 | 3.728 |
| 21 | 24.7 | 256 | 34 | 0.1338 | 3.604 |
| 22 | 25.6 | 309 | 41 | 0.1338 | 3.482 |
| 23 | 26.2 | 1899 | 313 | 0.1673 | 3.397 |
| 24 | 26.9 | 1588 | 183 | 0.1171 | 3.310 |
| 25 | 27.6 | 1357 | 224 | 0.1673 | 3.231 |
| 26 | 29.1 | 140 | 37 | 0.2676 | 3.069 |
| 27 | 29.5 | 145 | 29 | 0.2007 | 3.023. |

2. A process for the preparation of the δd-crystalline form of ivabradine hydrochloride of claim 1, wherein acetonitrile or a mixture of acetonitrile and water is preheated, ivabradine hydrochloride is added, the solution obtained is allowed to cool at room temperature, held at room temperature until crystallization is complete, and the crystals formed are dehydrated.

3. The process of claim 2, wherein the solution of ivabradine hydrochloride is seeded during the cooling step.

4. A solid pharmaceutical composition comprising as active ingredient the δd-crystalline form of ivabradine hydrochloride of claim 1, in combination with one or more pharmaceutically acceptable, inert, non-toxic carriers.

5. A method for treating a condition selected from angina pectoris, myocardial infarct and heart failure, such method comprising the step of administering to a living animal body, including a human, a therapeutically effective amount of δd-crystalline form of ivabradine hydrochloride of claim 1.

* * * * *